United States Patent [19]

Huff

[11] 4,150,158
[45] Apr. 17, 1979

[54] OXADIAZINDIONE DERIVATIVES USEFUL AS INSECTICIDES

[75] Inventor: Roger K. Huff, Wokingham, England

[73] Assignee: Imperial Chemical Industries Limited, London, England

[21] Appl. No.: 814,668

[22] Filed: Jul. 11, 1977

[30] Foreign Application Priority Data

Jul. 15, 1976 [GB] United Kingdom ............... 29540/76

[51] Int. Cl.$^2$ ..................... C07D 273/04; A01N 9/20
[52] U.S. Cl. ................... 424/248.57; 71/92; 544/67
[58] Field of Search ..................... 544/67; 424/248.57; 71/92

[56] References Cited

FOREIGN PATENT DOCUMENTS 2283133  3/1976  France ..................... 544/67

OTHER PUBLICATIONS

Tsuge et al., Chem. Abstracts, vol. 63, abst. No. 4299e (1965).
Tsuge et al., Chem. Abstracts, vol. 66, abst. No. 85552s (1967).
Singh et al., Chem. Abstracts, vol. 74, abst. No. 13114t (1971).
Singh et al., Chem. Abstracts, vol. 76, abst. No. 140743p (1972).
Etienne et al., Chem. Abstracts, vol. 76, abst. No. 140744q (1972).
Sheludyakov et al., Chem. Abstracts, vol. 78, abst. No. 29881j (1973).
Sridhara et al., Chem. Abstracts, vol. 84, abst. No. 74235 (1976).

*Primary Examiner*—John D. Randolph
*Attorney, Agent, or Firm*—Cushman, Darby & Cushman

[57] ABSTRACT

Insectically active oxadiazindione derivatives of the formula:

$$R^1-C(=N-N(R^2)-C(=O)-O-C(=O))$$

wherein $R^1$ is 2-chlorophenyl, 4-chlorophenyl, 2,6-dichlorophenyl, 3,5-dichlorophenyl, 2,6-difluorophenyl, 3-nitrophenyl, 3-trifluoromethylphenyl, 2-tolyl or 3,5-xylyl, and $R^2$ is phenyl or phenyl substituted by methyl, methoxy, chlorine, fluorine, or nitro, provided that at least one of $R^1$ and $R^2$ is a chloro-or fluoro-substituted phenyl group.

8 Claims, No Drawings

OXADIAZINDIONE DERIVATIVES USEFUL AS INSECTICIDES

This invention relates to oxadiazine derivatives useful as insecticides.

French Pat. No. 7,430,110 (publication no 2283133) discloses a group of compounds of general formula:

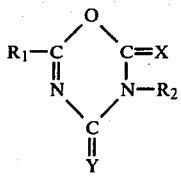

in which X and Y are independently selected from oxygen and sulphur; $R_1$ is selected from alkyl containing less than five carbon atoms and optionally substituted, alkoxy or mercapto containing less than five carbon atoms, disubstituted amino, and aryl which may optionally be substituted with alkyl, alkoxy, nitro or halogen; and $R_2$ is selected from alkyl containing less than twelve carbon atoms, and aryl which may optionally be substituted with alkyl, alkoxy, nitro or halogen; provided that $R_1$ and $R_2$ are not both alkyl. This group of compounds is said to be useful as herbicides (when X and Y are oxygen) or as fungicides (when X and Y are sulphur). There is no recitation or suggestion of any of the compounds of this group possessing any insecticidal properties.

We have discovered that within the broad class of compounds embraced by the above mentioned French patent there is a narrow class of compounds, the members of which have not previously been described and possess valuable insecticidal properties.

Accordingly the present invention provides compounds according to the formula:

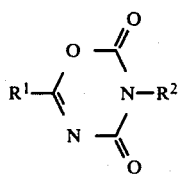

wherein $R^1$ is 2-chlorophenyl, 4-chlorophenyl, 2,6-dichlorophenyl, 3,5-dichlorophenyl, 2,6-difluorophenyl, 3-nitrophenyl, 3-trifluoromethylphenyl, 2-tolyl or 3,5-xylyl, and $R^2$ is phenyl or phenyl substituted by methyl, methoxy, chlorine, fluorine, or nitro, provided that at least one of $R^1$ and $R^2$ is a chloro-or fluoro-substituted phenyl group.

Preferred compounds within the group are those wherein $R^1$ is 2,6-dichlorophenyl or 2,6-difluorophenyl, or those wherein $R^2$ is chloro- or fluoro- substituted phenyl group. Especially preferred compounds are those wherein $R^1$ is a 2,6-difluorophenyl group and $R^2$ is a chloro- substituted phenyl group.

Particular examples of compounds embraced by this invention are those given in Table 1 which sets out the meaning of $R^1$ and $R^2$ for each compound together with its melting point.

TABLE 1

| Compound No | $R^1$ | $R^2$ | Melting point (° C.) |
| --- | --- | --- | --- |
| 1 | 4-chlorophenyl | phenyl | 213 |
| 2 | " | 3,4-dichlorophenyl | 204 |
| 3 | " | 4-chlorophenyl | 211 |
| 4 | " | 4-tolyl | 210 |
| 5 | " | 4-methoxyphenyl | 212 |
| 6 | " | 4-nitrophenyl | 180 |
| 7 | 2,6-difluorophenyl | 3,4-dichlorophenyl | 196–197 |
| 8 | " | 4-chlorophenyl | 192 |
| 9 | " | phenyl | 178 |
| 10 | " | 2,6-dichlorophenyl | 193 |
| 11 | " | 3-chlorophenyl | 144 |
| 12 | " | 4-fluorophenyl | 195 |
| 13 | 2,6-difluorophenyl | 4-tolyl | 175 |
| 14 | " | 4-methoxyphenyl | 185 |
| 15 | " | 3-fluorophenyl | 166 |
| 16 | " | 2-chlorophenyl | 168 |
| 17 | " | 2-fluorophenyl | 176 |
| 18 | 2-chlorophenyl | 4-chlorophenyl | 178 |
| 19 | " | 3,4-dichlorophenyl | 186 |
| 20 | 2-tolyl | 4-chlorophenyl | 190 |
| 21 | " | 3,4-dichlorophenyl | 189 |
| 22 | 3-nitrophenyl | 4-chlorophenyl | 194 |
| 23 | " | 3,4-dichlorophenyl | 202 |
| 24 | 3-trifluoromethylphenyl | 4-chlorophenyl | 179 |
| 25 | 3-trifluoromethylphenyl | 3,4-dichlorophenyl | 177 |
| 26 | 3,5-dichlorophenyl | 4-chlorophenyl | 211 |
| 27 | " | 3,4-dichlorophenyl | 209 |
| 28 | 3-nitrophenyl | 3-chlorophenyl | 190 |
| 29 | 3-trifluoromethylphenyl | 3-chlorophenyl | 181 |
| 30 | 3,5-dichlorophenyl | 3-chlorophenyl | 179 |
| 31 | 3,5-xylyl | 4-chlorophenyl | 184 |
| 32 | " | 3,4-dichlorophenyl | 182 |
| 33 | " | 3-chlorophenyl | 183 |
| 34 | 2,6-dichlorophenyl | 4-chlorophenyl | 193 |
| 35 | " | 3,4-dichlorophenyl | 178 |
| 36 | " | 3-chlorophenyl | 141 |
| 37 | 2,6-dichlorophenyl | 4-fluorophenyl | 193 |
| 38 | 2,6-difluorophenyl | 4-nitrophenyl | 196 |
| 39 | 2-chlorophenyl | 4-fluorophenyl | 159 |
| 40 | 2-tolyl | " | 202 |
| 41 | 3,5-dichlorophenyl | " | 194 |
| 42 | 3,5-xylyl | " | 183 |

Particularly useful compounds are those numbered 7 and 8 in the above Table, that is 3-(3,4-dichlorophenyl)-6-(2,6-difluorophenyl)-3,4-dihydro-2H-1,3,5-oxadiazin-2,4-dione and 3-(4-chlorophenyl)-6-(2,6-difluorophenyl)-3,4-dihydro-2H-1,3,5-oxadiazin-2,4-dione.

The invention compounds are distinguished from the teachings of the above mentioned French patent not only by the presence of valuable insecticidal properties, but also by the absence of any phytotoxic effects which would if present render the compounds of little use in combating insect pests of plants, particularly growing crops. This property of lack of herbicidal properties is very surprising in view of the fact that the French patent teaches that compounds falling within its scope and not having sulphur atoms present have notable herbicidal activity.

The nature of $R^1$ in the compounds appears to determine the presence or absence of the insecticidal properties. Thus in the compounds of the invention where $R^1$ is as given above the compounds have useful insecticidal properties. However, if $R^1$ is selected from phenyl, 3-tolyl, 4 tolyl, 3-methoxyphenyl, 4-methoxyphenyl or alkyl then the compounds are devoid of useful insecticidal activity.

The compounds of the invention may be prepared by reacting together an acyl isocyanate of the formula:

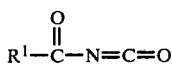

with an isocyanate of the formula:

$$R^2-N=C=O$$

wherein $R^1$ and $R^2$ have any of the meanings given hereinabove.

The process may be conveniently carried out by heating a mixture of the two reactants in the absence of a solvent or diluent at a temperature within the range 60° C. to 150° C. for a period of from about 30 minutes to about 30 hours.

A solvent or diluent for the reactants might be appropriate in certain circumstances, particularly where the product has a high melting point. Suitable solvents or diluents are those which do not hinder the progress of the reaction by encouraging side reactions, and which have a sufficiently high boiling point to permit the reactants to be heated to a suitable temperature. Examples of suitable solvents or diluents are polar aprotic solvents of the type exemplified by dimethyl sulphoxide, dimethylformamide, N,N-dimethylacetamide, and the like.

A preferred temperature range for preparing the compounds of the invention by the above process is 80° C. to 120° C., and a preferred period of reaction is from 1 to 10 hours.

Compounds of formula II which may be used in the preparation of the compounds of the invention are those wherein $R^1$ is 4-chlorophenyl, 3-nitrophenyl, 3-trifluoromethylphenyl, 2,6-dichlorophenyl, 2-chlorophenyl, 3,5-dichlorophenyl, 2,6-difluorophenyl, 3,5-xylyl or 2-tolyl.

Examples of compounds of formula III which may be reacted with compounds of formula II to give the invention compounds include those where $R^2$ is phenyl, nitro-substituted or halo-substituted or methyl-substituted or methoxy-substituted phenyl such as 4-nitrophenyl, 2-,3- or 4-chlorophenyl, 2,6-or 3,4-dichlorophenyl, 2-, 3- or 4-fluorophenyl, 4-tolyl and 4-methoxyphenyl.

Other methods of preparing the invention compounds may be contemplated involving for example the condensation of a compound of formula:

where X is a halo or alkoxy group with a compound of formula III or the condensation of a compound of formula

where R is an alkyl group with a compound of formula II, or the condensation of a compound of formula IV with a compound of formula V. As stated above the compounds of the invention exhibit useful insecticidal properties, and may be utilised to combat insect pests of plants, stored products, and the like. They may be particularly usefully employed in agriculture and horticulture when formulated into compositions with various agriculturally and horticulturally acceptable diluent or carrier materials.

In a further aspect therefore the present invention provides pesticidal compositions comprising as an active ingredient a compound of formula I wherein $R^1$ and $R^2$ have any of the meanings given hereinabove, together with a diluent.

The compositions may be in the form of dusting powders wherein the active ingredient is mixed with a solid diluent or carrier, for example, kaolin, bentonite, kieselguhr, or talc, or they may be in the form of granules, wherein the active ingredient is absorbed on a porous granular material, for example, pumice.

Alternatively the compositions may be in the form of liquid preparations to be used as dips or sprays, which are generally aqueous dispersions or emulsions of the active ingredients in the presence of one or more known wetting agents, dispersing agents or emulsifying agents. These compositions are prepared by dissolving the active ingredient in a suitable solvent, for example, a ketonic solvent such as diacetone alcohol, and adding the mixture so obtained to water which may contain one or more known wetting, dispersing or emulsifying agents.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage to be capable of dilution with water in order to form aqueous preparations which remain homogeneous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient or ingredients may be used.

The compositions of the present invention may, if desired, also comprise in addition to a compound of the present invention, at least one other biologically-active ingredient, for example an insecticide, or a fungicide.

In use the compositions are applied to the pests, to the locus of the pests, to the habitat of the pests, or to growing plants liable to infestation by the pests, by any of the known means of applying pesticidal compositions for example, by dusting or spraying.

The compounds of the invention and compositions comprising them are toxic to a variety of insect pests including, for example, the following:
*Aedes aegypti* (mosquitos)
*Dysdercus fasciatus* (capsids)
*Pieris brassicae* (white butterfly, larvae)
*Phaedon cochleariae* (mustard beetle)
*Plutella xylostella* (diamond back moth, larvae)

They are particularly effective in combating the larval forms of lepidopterous and coleopterous pests which feed on growing crops.

The invention is illustrated by the following examples.

EXAMPLE 1

This Example illustrates the preparation of 2,6-difluorobenzoyl isocyanate.

Oxalyl chloride (5.5 g) was added slowly to a suspension of 2,6-difluorobenzamide (6.0 g) in 1,2-dichloroethane maintained at a temperature within the range −10° to −5° C. When the addition was complete the mixture was allowed to warm to the ambient temperature, and then gradually heated to the reflux temperature and maintained thereat for a period of 16 hours. The solvent was then removed by evaporation under reduced pressure and the residual oil purified by distillation to yield 2,6-difluorobenzoyl isocyanate, b.p. 60°-61°/0.7 mm.

EXAMPLE 2

By a process similar to that illustrated in Example 1 the following acylisocyanates were prepared from the corresponding amides.
3-nitrobenzoyl isocyanate, b.p. 126° C./0.5 mm.
2-chlorobenzoyl isocyanate, b.p. 67°-68° C./0.2 mm.
4-chlorobenzoyl isocyanate, b.p. 114° C./14 mm.
3-trifluoromethylbenzoyl isocyanate, b.p. 84° C./1.0 mm.
2-toluoyl isocyanate, b.p. 69° C./0.7 mm.
3,5-dimethylbenzoyl isocyanate, b.p. 72°-73°/0.08 mm.
2,6-dichlorobenzoyl isocyanate, b.p. 110°/0.8 mm.

EXAMPLE 3

This example illustrates the preparation of 3-(3,4-dichlorophenyl)-6-(2,6-difluorophenyl)-3,4-dihydro-2H-1,3,5-oxadiazin-2,4-dione (compound no 7, Table 1) of formula:

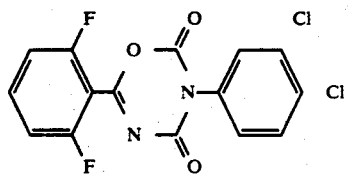

A mixture of freshly prepared 2,6-difluorobenzoyl isocyanate (1.85 g) and 3,4-dichlorophenyl isocyanate (1.89 g) is heated at 120° C. for a period of 16 hours, and then cooled. Recrystallisation of the solid which was obtained from ethyl acetate yielded 3-(3,4-dichlorophenyl)-6-(2,6-difluorophenyl)-3,4-dihydro-2H-1,3,5-oxadiazin-2,4-dione, white crystals, m.p. 196°-197° C.

EXAMPLE 4

The procedure of Example 3 was used to prepare the other compounds of Table 1 from the appropriate starting materials as follows:
3-phenyl-6-(4-chlorophenyl)-3,4-dihydro-2H-1,3,5-oxadiazin-2,4-dione (Compound no 1, Table 1; m.p. 213° C.), from 4-chloro-benzoyl isocyanate and phenyl isocyanate;
3-(3,4-dichlorophenyl)-6-(4-chlorophenyl)-3,4-dihydro-2H-1,3,5-oxadiazin-2,4-dione (Compound no 2, Table 1; m.p. 204° C.), from 4-chlorobenzoyl isocyanate and 3,4-dichlorophenyl isocyanate;
3-(4-chlorophenyl)-6-(4-chlorophenyl)-3,4-dihydro-2H-1,3,5-oxadiazin-2,4-dione (Compound no 3 Table 1; m.p. 211° C.), from 4-chlorobenzoyl isocyanate and 4-chlorophenyl isocyanate;
3-(4-tolyl)-5(4-chlorophenyl)-3,4-dihydro-2H-1,3,5-oxadiazin-2,4-dione (Compound no 4, Table 1; m.p. 210° C.), from 4-chlorobenzoyl isocyanate and 4-tolyl isocyanate;
3-(4-methoxyphenyl)-6-(4-chlorophenyl)-3,4-dihydro-2H-1,3,5-oxadiazin-2,4-dione (Compound no 5, Table 1; L m.p. 212° C.), from 4-chlorobenzoyl isocyanate and 4-methoxyphenyl isocyanate;
3-(4-nitrophenyl)-6-(4-chlorophenyl-3,4-dihydro-2H-1,3,5-oxadiazin-2,4-dione (Compound no 6, Table 1; m.p. 180° C.), from 4-chlorobenzoyl isocyanate and 4-nitrophenyl isocyanate;
3-(3,4-dichlorophenyl)-6-(2,6-difluorophenyl)-3,4-dihydro-2H-1,3,5-oxadiazin-2,4-dione (Compound no 7, Table 1; m.p. 196°-197° C., from 2,6-difluorobenzoyl isocyanate and 3,4-dichlorophenyl isocyanate;
3-(4-chlorophenyl)-6-(2,6-difluorophenyl)-3,4-dihydro-2H-1,3,5-oxadiazin-2,4-dione (Compound no 8, Table 1; m.p. 192° C.), from 2,6-difluorobenzoyl isocyanate and 4-chlorophenyl isocyanate;
3-phenyl-6-(2,6-difluorophenyl)-3,4-dihydro-2H-1,3,5-oxadiazin-2,4-dione (Compound no 9, Table 1; m.p. 178° C.), from 2,6-difluorobenzoyl isocyanate and phenyl isocyanate;
3-(2,6-dichlorophenyl)-6-(2,6-difluorophenyl)-3,4-dihydro-2H-1,3,5-oxadiazin-2,4-dione (Compound no 10, Table 1; m.p. 193° C.), from 2,6-difluorobenzoyl isocyanate and 2,6-dichlorophenyl isocyanate;
3-(3-chlorophenyl)-6-(2,6-difluorophenyl)-3,4-dihydro-2H-1,3,5-oxadiazin-2,4-dione (Compound no 11, Table 1; m.p. 144° C.), from 2,6-difluorobenzoyl isocyanate and 3-chlorophenyl isocyanate;
3-(4-fluorophenyl)-6-(2,6,difluorophenyl)-3,4-dihydro-2H-1,3,5-oxadiazin-2,4-dione (Compound no 12, Table 1; m.p. 195° C.), from 2,6-difluorobenzoyl isocyanate and 4-fluoro phenyl isocyanate;
3-(4-tolyl)-6-(2,6-difluorophenyl)-3,4-dihydro-2H-1,3,5-oxadiazin-2,4-dione (Compound no 13, Table 1; m.p. 175° C.), from 2,6-difluorobenzoyl isocyanate and 4-tolyl isocyanate;
3-(4-methoxyphenyl)-6-(2,6-difluorophenyl)-3,4-dihydro-2H-1,3,5-oxadiazin-2,4-dione (Compound no 14, Table 1; m.p. 185° C.), from 2,6-difluorobenzoyl isocyanate and 4-methoxyphenyl isocyanate;
3-(3-fluorophenyl)-6-(2,6-difluorophenyl)-3,4-dihydro-2H-1,3,5-oxadiazin-2,4-dione (Compound no 15, Table 1; m.p. 166° C.), from 2,6-difluorobenzoyl isocyanate and 3-fluorobenzyl isocyanate;
3-(2-chlorophenyl)-6-(2,6-difluorophenyl)-3,4-dihydro-2H-1,3,5-oxadiazin-2,4-dione (Compound no 16, Table 1; m.p. 168° C.), from 2,6-difluorobenzoyl isocyanate and 2-chlorophenyl isocyanate;
3-(2-fluorophenyl)-6-(2,6-difluorophenyl)-3,4-dihydro-2H-1,3,5-oxadiazin-2,4-dione (Compound no 17, Table 1; m.p. 176° C.), from 2,6-difluorobenzoyl isocyanate and 2-fluorophenyl isocyanate;
3-(4-chlorophenyl)-6-(2-chlorophenyl)-3,4-dihydro-2H-1,3,5-oxadiazin-2,4-dione (Compound no 18, Table 1; m.p. 178° C.), from 2-chlorobenzoyl isocyanate and 4-chlorophenyl isocyanate;
3-(3,4-dichlorophenyl)-6-(2-chlorophenyl)-3,4-dihydro-2H-oxadiazin-2,4-dione (Compound no 19, Table 1; m.p. 186° C.), from 2-chlorobenzoyl isocyanate and 3,4-dichlorophenyl isocyanante;
3-(4-chlorophenyl)-6-(2-tolyl)-3,4-dihydro-2H-oxadiazin-2,4-dione (Compound no 20, Table 1; m.p. 190° C.), from 2-toluyl isocyanate and 4-chlorophenyl isocyanate;
3-(3,4-dichlorophenyl)-6-(2-tolyl)-3,4-dihydro-2H-oxadiazin-2,4-dione (Compound no 21, Table 1; m.p. 189° C.), from 2-toluyl isocyanate and 3,4-dichlorophenyl isocyanate;
3-(4-chlorophenyl)-6-(3-nitrophenyl)-3,4-dihydro-2H-oxadiazin-2,4-dione (Compound no 22 Table 1; m.p. 194° C.), from 3-nitrobenzoyl isocyanate and 4-chlorophenyl isocyanate;

3-(3,4-dichlorophenyl)-6-(3-nitrophenyl)-3,4-dihydro-2H-oxadiazin-2,4-dione (Compound no 23, Table 1; m.p. 202° C.), from 3-nitrobenzoyl isocyanate and 3,4-dichlorophenyl isocyanate;

3-(4-chlorophenyl)-6-(3-trifluoromethylphenyl)-3,4-dihydro-2H-oxadiazin-2,4-dione (Compound no 24, Table 1; m.p. 179° C.), from 3-trifluoromethylbenzoyl isocyanate and 4-chlorophenyl isocyanate;

3-(3,4-dichlorophenyl)-6-(3-trifluoromethylphenyl)-3,4-dihydro-2H-oxadiazin-2,4-dione (Compound no 25, Table 1; m.p. 177° C.), from 3-trifluoromethylbenzoyl isocyanate and 3,4-dichlorophenyl isocyanate;

3-(4-chlorophenyl)-6-(3,5-dichlorophenyl)-3,4-dihydro-2H-oxadiazin-2,4-dione (Compound no 26, Table 1; m.p. 211° C.), from 3,5-dichlorobenzoyl isocyanate and 4-chlorophenyl isocyanate;

3-(3,4-dichlorophenyl)-6-(3,5-dichlorophenyl)-3,4-dihydro-2H-oxadiazin-2,4-dione (Compound no 27, Table 1; m.p. 209° C.), from 3,5-dichlorobenzoyl isocyanate and 3,4-dichlorophenyl isocyanate;

3-(3-chlorophenyl)-6-(3-nitrophenyl)-3,4-dihydro-2H-oxadiazin-2,4-dione (Compound no 28, Table 1; m.p. 190° C.), from 3-nitrobenzoyl isocyanate and 3-chlorophenyl isocyanate;

3-(3-chlorophenyl)-6-(3-trifluoromethylphenyl)-3,4-dihydro-2H-oxadiazin-2,4-dione (Compound no 29, Table 1; m.p. 181° C.), from 3-trifluoromethylbenzoyl isocyanate and 3-chlorophenyl isocyanate;

3-(3-chlorophenyl)-6-(3,5-dichlorophenyl)-3,4-dihydro-2H-oxadiazin-2,4-dione (Compound no 30, Table 1; m.p. 179° C.), from 3,5-dichlorobenzoyl isocyanate and 3-chlorophenyl isocyanate.

3-(4-chlorophenyl)-6-(3,5-xylyl)-3,4-dihydro-2H-1,3,5-oxadiazin-2,4-dione (Compound no 31, Table 1; m.p. 184° C.), from 3,5-dimethylbenzoyl isocyanate and 4-chlorophenyl isocyanate;

3-(3,4-dichlorophenyl)-6-(3,5-xylyl)-3,4-dihydro-2H-1,3,5-oxadiazin-2,4-dione (Compound no 32, Table 1; m.p. 182° C.), from 3,5-dimethylbenzoyl isocyanate and 3,4-dichlorophenyl isocyanate;

3-(3-chlorophenyl)-6-(3,5-xylyl)-3,4-dihydro-2H-1,3,5-oxadiazin-2,4-dione (Compound no 33, Table 1; m.p. 183° C.), from 3,5-dimethylbenzoyl isocyanate and 3-chlorophenyl isocyanate;

3-(4-chlorophenyl)-6-(2,6-dichlorophenyl)-3,4-dihydro-2H-1,3,5-oxadiazin-2,4-dione (Compound no 34, Table 1; m.p. 193° C.), from 2,6-dichlorobenzoyl isocyanate and 4-chlorophenyl isocyanate;

(3,4-dichlorophenyl)-6-(2,6-dichlorophenyl)-3,4-dihydro-2H-1,3,5-oxadiazin-2,4-dione (Compound no 35, Table 1; m.p. 178° C.), from 2,6-dichlorobenzoyl isocyanate and 3,4-dichlorophenyl isocyanate;

3-(3-chlorophenyl)-6-(2,6-dichlorophenyl)-3,4-dihydro-2H-1,3,5-oxadiazin-2,4-dione (Compound no 36, Table 1; m.p. 141° C.), from 2,6-dichlorobenzoyl isocyanate and 3-chlorophenyl isocyanate;

3-(4-fluorophenyl)-6-(2,6-dichlorophenyl)-3,4-dihydro-2H-1,3,5-oxadiazin-2,4-dione (Compound no 37, Table 1; m.p. 193° C.), from 2,6-dichlorobenzoyl isocyanate and 4-fluorophenyl isocyanate;

3-(4-nitrophenyl)-6-(2,6-difluorophenyl)-3,4-dihydro-2H-1,3,5-oxadiazin-2,4-dione (Compound no 38, Table 1; m.p. 196° C.), from 2,6-difluorobenzoyl isocyanate and 4-nitrophenyl isocyanate;

3-(4-fluorophenyl)-6-(2-chlorophenyl)-3,4-dihydro-2H-1,3,5-oxadiazin-2,4-dione (Compound no 39, Table 1; m.p. 159° C.), from 2-chlorobenzoyl isocyante and 4-fluorophenyl isocyanate;

3-(4-fluorophenyl)-6-(2-tolyl)-3,4-dihydro-2H-1,3,5-oxadiazin-2,4-dione (Compound no 40, Table 1 m.p. 202° C.) from 2-toluyl isocyanate and 4-fluorophenyl isocyanate;

3-(4-fluorophenyl)-6-(3,5-dichlorophenyl)-3,4-dihydro-2H-1,3,5-oxadiazin-2,4-dione (Compound no 41, Table 1; m.p. 194° C.), from 3,5-dichlorobenzoyl isocyanate and 4-fluorophenyl isocyanate; and 3-(4-fluorophenyl)-6-(3,5-xylyl)-3,4-dihydro-2H-1,3,5-oxadiazin-2,4-dione (Compound no 42, Table 1; m.p. 183° C.), from 3,5-dimethylbenzoyl isocyanate and 4-fluorophenyl isocyanate.

EXAMPLE 5

The insecticidal properties of the invention compounds are illustrated by the following tests.

(a) Test with *Dysdercus fasciatus*

Ten fourth instar nymphs are placed in a dish (diameter 10 cm) with 20 cotton seeds and a pad of moistened cotton wool. The dish and its contents are sprayed for 2-3 seconds with a preparation containing 1,000 p.p.m. of the compound under test. The preparation is made up by dissolving the compound in the minimum quantity of a mixture of 1 part by volume of ethyl alcohol and 1 part by volume of acetone and diluting the solution thus obtained by water to obtain the required concentration. The dish is kept at 25° C. and 60% relative humidity for 13 days and is covered with aluminum foil after 6 days. The mortality of the nymphs is assessed at the end of this period.

(b) Test with *Aedes aegypti*

Five half grown third or fourth instar larvae are placed in a beaker containing 25 ml of tap water. A preparation of the chemical (prepared as in (a) above) is added to give a final concentration of 10 p.p.m. of the chemical. The number of dead larvae are assessed after 24 hours.

(c) Test with *Plutella xylostella*

Leaves are cut from a mustard plant which has been sprayed to dip point with a preparation of the test chemical (prepared as in (a) above) and infested with 10 half grown fourth instar larvae. The mortality is assessed after 13 days.

(d) Test with *Phaedon cochleariae*

Mustard seedlings are sprayed as in (c) above and infested with 10 fourth instar larvae. The mortality is assessed after 13 days.

The results obtained in tests (a), (b), (c) and (d) set out for each compound tested in Table II. The assessment is expressed in integers which range from 0 to 3, in which 0 represents less than 30% mortality
1 represents 30 to 49% mortality
2 represents 50 to 95% mortality
3 represents 96 to 100% mortality A dash (-) in Table II indicates that no test was carried out.

TABLE II

| Compound No | Test (a) | (b) | (c) | (d) | Compound No | Test (a) | (b) | (c) | (d) |
|---|---|---|---|---|---|---|---|---|---|
| 1 | 0 | 2 | — | 0 | 22 | — | — | 3 | 0 |
| 2 | 0 | 2 | — | 0 | 23 | — | — | 2 | 0 |
| 3 | 0 | 3 | — | 0 | 24 | — | — | 2 | 0 |
| 4 | 0 | 0 | 3 | 0 | 25 | — | — | 3 | 0 |
| 5 | 0 | 0 | 2 | 0 | 26 | 1 | — | 2 | 1 |

TABLE II-continued

| Compound No | Test (a) | Test (b) | Test (c) | Test (d) | Compound No | Test (a) | Test (b) | Test (c) | Test (d) |
|---|---|---|---|---|---|---|---|---|---|
| 6 | 0 | 0 | 2 | 0 | 27 | 0 | — | 2 | 0 |
| 7 | 3 | 3 | 3 | 3 | 28 | 2 | — | 2 | 0 |
| 8 | 3 | 3 | 2 | 3 | 29 | 2 | — | 2 | 0 |
| 9 | 3 | 3 | 1 | 0 | 30 | 1 | — | 0 | 0 |
| 10 | 0 | 3 | 1 | 1 | 31 | 2 | — | 2 | 0 |
| 11 | 3 | — | 2 | 3 | 32 | 3 | — | 2 | 0 |
| 12 | 3 | 3 | 2 | 3 | 33 | 1 | — | 0 | 2 |
| 13 | 3 | 1 | 0 | 2 | 34 | — | — | 2 | 0 |
| 14 | 0 | 3 | 1 | 1 | 35 | — | — | 3 | 0 |
| 15 | 3 | 3 | 0 | 0 | 36 | — | — | 2 | 0 |
| 16 | 0 | 3 | 0 | 0 | 37 | — | — | 1 | 0 |
| 17 | 3 | 3 | 0 | 0 | 38 | 2 | — | 2 | 2 |
| 18 | — | — | 1 | 3 | 39 | 0 | — | 2 | 0 |
| 19 | — | — | 0 | 3 | 40 | 0 | — | 2 | 0 |
| 20 | — | — | 0 | 2 | 41 | 0 | — | 2 | 0 |
| 21 | — | — | 2 | 3 | 42 | 1 | — | 2 | 0 |

I claim:

1. An insecticidally active oxidiazine derivative of formula:

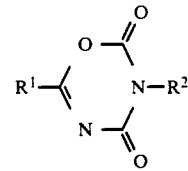

wherein $R^1$ is 2-chlorophenyl, 4-chlorophenyl, 2,6-dichlorophenyl, 3,5-dichlorophenyl, 2,6-difluorophenyl, 3-nitrophenyl, 3-trifluoromethylphenyl, 2-tolyl or 3,5-xylyl, and $R^2$ is phenyl or phenyl substituted by methyl, methoxy, chlorine, fluorine, or ntiro, provided that at least one of $R^1$ and $R^2$ is a chloro-or fluoro-substituted phenyl group.

2. A compound as claimed in claim 1 wherein $R^1$ is 2,6-dichlorophenyl or 2,6-difluorophenyl.

3. A compound as claimed in claim 1 wherein $R^2$ is a chloro- or fluoro-substituted phenyl group.

4. A compound as claimed in claim 1 wherein $R^1$ is 2,6-difluorophenyl and $R^2$ is a chloro-substituted phenyl group.

5. 3-(3,4-dichlorophenyl)-6-(2,6-difluorophenyl)-3,4-dihydro-2H-1,3,5-oxadiazin-2,4-dione.

6. 3-(3-chlorophenyl)-6-(2,6-difluorophenyl)-3,4-dihydro-2H-1,3,5-oxidiazin-2,4-dione.

7. An insecticidal composition comprising an insecticidally effective amount of a compound according to claim 1 together with a diluent.

8. A method of combating insect pests at a locus which comprises applying an effective amount of a composition according to claim 7 to the locus.

* * * * *